(12) United States Patent
Dasbach et al.

(10) Patent No.: US 12,070,590 B2
(45) Date of Patent: Aug. 27, 2024

(54) INJECTION DEVICE

(71) Applicant: Sanofi, Paris (FR)

(72) Inventors: Uwe Dasbach, Frankfurt am Main (DE); Thomas Kemp, Cambridgeshire (GB); Hugo Revellat, Cambridgeshire (GB); Jim Bradford, Cambridgeshire (GB)

(73) Assignee: Sanofi, Paris (FR)

( * ) Notice: Subject to any disclaimer, the term of this patent is extended or adjusted under 35 U.S.C. 154(b) by 865 days.

(21) Appl. No.: 17/266,748

(22) PCT Filed: Aug. 13, 2019

(86) PCT No.: PCT/EP2019/071768
§ 371 (c)(1),
(2) Date: Feb. 8, 2021

(87) PCT Pub. No.: WO2020/035513
PCT Pub. Date: Feb. 20, 2020

(65) Prior Publication Data
US 2021/0316082 A1 Oct. 14, 2021

(30) Foreign Application Priority Data
Aug. 13, 2018 (EP) ..................... 18306113

(51) Int. Cl.
*A61M 5/20* (2006.01)
*A61M 5/24* (2006.01)
*A61M 5/32* (2006.01)

(52) U.S. Cl.
CPC ............ *A61M 5/3271* (2013.01); *A61M 5/24* (2013.01); *A61M 5/322* (2013.01); *A61M 5/326* (2013.01);
(Continued)

(58) Field of Classification Search
CPC ...... A61M 5/3271; A61M 5/24; A61M 5/322; A61M 5/326; A61M 5/3243;
(Continued)

(56) References Cited

U.S. PATENT DOCUMENTS 6,544,234 B1 * 4/2003 Gabriel ............... A61M 5/3271
604/218
9,656,021 B2 * 5/2017 Brereton ............. A61M 5/3204
(Continued)

FOREIGN PATENT DOCUMENTS

CN 1874810 12/2006
CN 103957969 7/2014
(Continued)

OTHER PUBLICATIONS

PCT International Preliminary Report on Patentability in International Application No. PCT/EP2019/071768, dated Feb. 16, 2021, 7 pages.
(Continued)

*Primary Examiner* — Nathan R Price
*Assistant Examiner* — Tania Ismail
(74) *Attorney, Agent, or Firm* — Fish & Richardson P.C.

(57) ABSTRACT

The present disclosure relates to an injection device including: a housing; a carrier disposed within the housing for holding a syringe that has a needle at one end; a needle sleeve located within the housing and being axially moveable with respect to the housing between an extended position and a retracted position; a biasing element configured to bias the needle sleeve towards the extended position; and a locking mechanism configured to lock the needle sleeve in the extended position after use of the injection device, the locking mechanism comprising; a first locking member provided on and projecting from the carrier; and a second locking member comprising a deflectable arm pro-
(Continued)

vided on the needle sleeve and moveable between a relaxed position and a deflected position.

20 Claims, 7 Drawing Sheets

(52) U.S. Cl.
CPC ... *A61M 2005/2073* (2013.01); *A61M 5/3243* (2013.01); *A61M 2005/3247* (2013.01); *A61M 2005/3254* (2013.01); *A61M 2005/3261* (2013.01); *A61M 2005/3267* (2013.01); *A61M 2005/3268* (2013.01)

(58) Field of Classification Search
CPC .. A61M 2005/3247; A61M 2005/3254; A61M 2005/2073; A61M 2005/3261; A61M 2005/3267; A61M 2005/3268
See application file for complete search history.

(56) References Cited

U.S. PATENT DOCUMENTS

| | | | |
|---|---|---|---|
| 2007/0073232 | A1 | 3/2007 | Pickhard |
| 2009/0270804 | A1 | 10/2009 | Mesa et al. |
| 2016/0106920 | A1 | 4/2016 | Stefansen |

FOREIGN PATENT DOCUMENTS

| | | |
|---|---|---|
| CN | 106029153 | 10/2016 |
| CN | 107666926 | 2/2018 |
| EP | 1138338 | 10/2001 |
| EP | 2489380 | 8/2012 |
| EP | 3338840 | 6/2018 |
| JP | 2013-529987 | 7/2013 |
| JP | 2013-534164 | 9/2013 |
| JP | 2015-520643 | 7/2015 |
| JP | 2016-523672 | 8/2016 |
| JP | 2018-516684 | 6/2018 |
| WO | WO 2012/000834 | 1/2012 |
| WO | WO 2012/000873 | 1/2012 |
| WO | WO 2012/022810 | 2/2012 |
| WO | WO 2013/050477 | 4/2013 |
| WO | WO 2015/004052 | 1/2015 |
| WO | WO 2015/092041 | 6/2015 |
| WO | WO 2016/193352 | 12/2016 |
| WO | WO 2016/193374 | 12/2016 |
| WO | WO 2017/046556 | 3/2017 |

OTHER PUBLICATIONS

PCT International Search Report and Written Opinion in International Application No. PCT/EP2019/071768, dated Nov. 20, 2019, 9 pages.

* cited by examiner

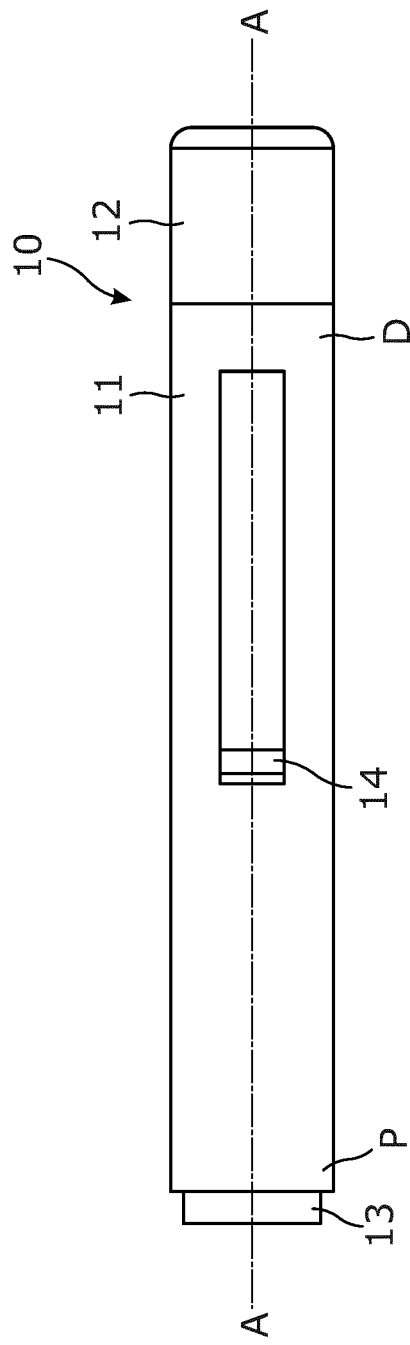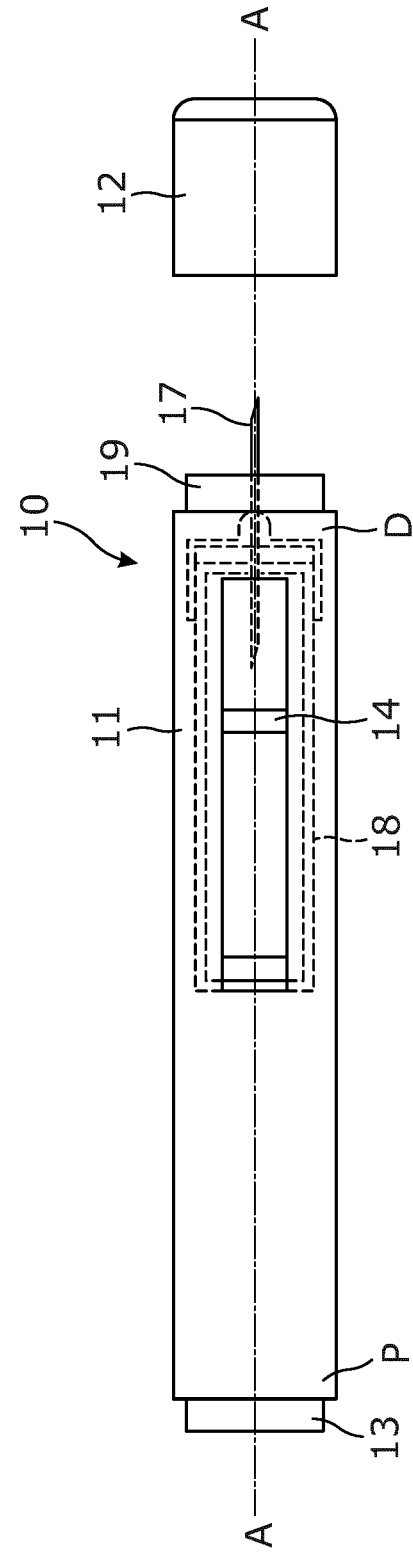
Figure 1A
Figure 1B

INJECTION DEVICE

CROSS REFERENCE TO RELATED APPLICATIONS

The present application is the national stage entry of International Patent Application No. PCT/EP2019/071768, filed on Aug. 13, 2019, and claims priority to Application No. EP 18306113.4, filed on Aug. 13, 2018, the disclosures of which are incorporated herein by reference.

TECHNICAL FIELD

The present disclosure relates to an injection device and to a method of actuating an injection device and a method of assembly of an injection device.

BACKGROUND

Injection devices, such as auto-injectors, are known in the art for dispensing a medicament to the injection site of a patient. Such injection devices often comprise a body and a cap, a needle syringe located in the body and the cap removably attached to the body to shield the needle of the needle syringe. To dispense the medicament, the cap is first removed from the body to expose the needle. The needle is then inserted into the body of the patient at the injection site to dispense the medicament.

It is important to prevent access to the needle after the injection has occurred. A moveable needle sleeve and locking means can be provided to ensure that the needle is covered after the medicament has been dispensed and that access to the needle is restricted; this prevents the sharp needle from causing injury and can also act as an indicator that the injection device has already been used.

SUMMARY

The present disclosure provides an improved injection device.

According to a first embodiment there is an injection device comprising: a housing; a carrier disposed within the housing for holding a syringe that has a needle at one end; a needle sleeve located within the housing and being axially moveable with respect to the housing between an extended position and a retracted position; a biasing element configured to bias the needle sleeve towards the extended position; the injection device comprising a locking mechanism configured to lock the needle sleeve in the extended position after use of the injection device, the locking mechanism comprising; a first locking member provided on and projecting from the carrier; and a second locking member comprising a deflectable arm provided on the needle sleeve and moveable between a relaxed position and a deflected position; wherein the housing includes an inwardly projecting boss which engages the second locking member and moves the second locking member into the deflected position as the needle sleeve is moved to the retracted position; the first and second locking members configured such that the first locking member is out of engagement with the second locking member when the second locking member is in the deflected position; and the first and second locking members configured such that the second locking member blocks the first locking member when the second locking member is in the relaxed position and the needle sleeve is in the extended position, thereby preventing movement of the needle sleeve back into the retracted position.

Preventing the movement of the needle sleeve back into the retracted position may improve the safety of the device as access to the needle can be restricted once the injection has occurred. This may also act as an indicator that the injection device has already been used, furthermore it can avoid accidental injury. The mechanism as described above may be particularly beneficial when a syringe with a short needle is required.

'Short' when referred to in this specification may refer to a needle length of less than about 12.5 mm, typically as an example about 6 mm, however it can be appreciated that the injection device described in this specification can also be used for a needle length greater than or equal to 12.5 mm. The length of the needle can be measured from the distal end of the syringe glass to the tip of the needle.

The terms distal and proximal as used herein refer to directions relative to the injection device. The term "distal" refers to a location that is relatively closer to a site of injection, and the term "proximal" refers to a location that is relatively further away from the injection site.

There are a number of benefits to using a short needle in an injection device; the overall size of the device is reduced in comparison to devices with longer length needles, the injection time can be improved, more viscous fluids can be injected, storage loads and stopper impact forces can be reduced and a thinner gauge needle can be used without compromising the injection time. A thinner gauge needle may also mean that there is less pain for a user and could be particularly beneficial in paediatric applications.

In one embodiment the needle sleeve may extend further out from the housing in the extended position than in the retracted position. In a further embodiment the needle sleeve may be moveable between three positions, a start position, the retracted position and the extended position, wherein the needle sleeve may extend further out from the housing in the extended position than in the start position, and may extend further out from the housing in the start position than in the retracted position.

In one embodiment, the needle sleeve is retractable between the housing and the carrier.

In one embodiment the deflectable arm may have a first end fixedly attached to the rest of the needle shield and a second, free end remote from the first end.

The injection device being moveable between three positions may aid the priming of the locking mechanism to be carried out during assembly of the device by machinery as opposed to manually. However it can be appreciated that the locking mechanism could be primed by a user before they actuate the injection device. For those who are elderly or infirm, or for those who are in a rush or require easier actuation of the device, simplification of actuating the injection device by priming the locking mechanism during the assembly stage is desirable.

In one embodiment, the first locking member comprises a protrusion.

In one embodiment when the needle sleeve is in the start position the deflectable arm may be in the relaxed position and the first locking member may be disposed distally of the free end of the deflectable arm.

Each arm may be deflectable circumferentially. However, a skilled person will recognize that in other embodiments the or each arm may be deflectable in an alternative direction, for example, being deflectable radially or tangentially.

In one embodiment the first and second locking members may be axially aligned when the second locking member is in the relaxed position but are out of axial alignment when the second locking member is in the deflected position. This may enable the first locking member to move past the second locking member when the second locking member is in the deflected position, this can provide a means for the second locking member to engage the first locking member in the start position but also to block the second locking member when the second locking member is in the relaxed position.

In one embodiment the deflectable arm may be deflectable laterally with respect to the axial direction of the injection device when the second locking portion is engaged by the inwardly projecting boss of the housing. Lateral deflection of the deflectable arm may aid simple assembly due to the alignment of particular components but also may enable the second locking member to engage with the first locking member when the second locking member is in the relaxed position.

The second locking member may be a pair of deflectable arms, it may be a single deflectable arm which is biased against a surface of the needle sleeve or alternative component. It can be appreciated that the second locking member may also be a pair of pivotable arms, the arms can be rigid and comprise a series of joints. There may also only be one pivotable arm biased against a fixed surface of the injection device, for example a surface of the needle sleeve. The second locking member may be directed in a proximal direction; however it can be appreciated that the second locking member may also be directed in a distal direction. The deflectable arm may be substantially linear and the free end of the deflectable arm may extend in a distal direction.

It may be beneficial for the second locking member to be a pair of deflectable arms; the equal force of each deflectable arm in the relaxed position on the first locking member may hold or block the first locking member more easily.

In one embodiment, the or each arm may be deflectable circumferentially with respect to the housing. However, a skilled person will recognise that in other embodiments the or each arm may be deflectable in an alternative direction, for example, being deflectable radially or tangentially with respect to the housing.

In one embodiment the injection device may further comprise a removable cap. One advantage of the cap is that it may shield the needle when not in use, helping to ensure that the needle remains sterile before use. The cap may also reduce the risk of accidental actuation of the injection device, for example when the device is dropped. When the cap is on the device, interlocking portions of the cap may engage with corresponding interlocking portions on the needle sleeve preventing accidental depression of the needle sleeve before the cap is removed.

In one embodiment the first locking member can comprise a T shaped boss projecting from the carrier. The first locking member may have a relative narrow portion and a relative wider portion, the first locking member may be at least substantially rigid. The boss may project inwardly or outwardly of the carrier, inward being towards the central axis of the injection device.

A T shaped boss may be advantageous to the performance of the locking mechanism. The head of the T may be easily held or blocked by the second locking member while still being able to move past the second locking member when the second locking member is in the deflected position. A T shaped boss can also be easily manufactured to be part of the carrier.

In one embodiment the inwardly projecting boss of the housing may be tapered or shaped like an arrow head, pointing in a distal direction. It can be appreciated however that any shape which can forcibly move the second locking member of the needle sleeve into the deflected position may be suitable.

A tapered or arrow like shape to the inwardly projecting boss may enable the inwardly projecting boss to gradually force the second locking member into the deflected position and gradually release the second locking member into the relaxed position. This gradual movement between positions can provide less force on the second locking members and reduce the likelihood of damage or elastic deformation.

In one embodiment the first locking member may comprise at least one rigid portion and the second locking member may comprise at least one flexible portion. The combination of rigid and flexible portions can also provide less force on the locking mechanism and reduce the likelihood of damage or elastic deformation to the locking mechanism.

In one embodiment the injection device may further comprise a syringe having a needle at one end. The syringe may contain a medicament.

In one embodiment, the injection device may be an auto-injector.

In one embodiment there is a method of assembling an injection device which may comprise the following steps: insert a syringe having a needle into the carrier; move the needle sleeve relative to the housing in a proximal direction of the device to a first assembly position wherein the inwardly projecting boss of the housing engages the second locking member of the needle sleeve and moves the second locking member from the relaxed position into the deflected position;

move the carrier into the housing in a distal direction to a second assembly position in which the second locking member is in the deflected position, the first locking member is disposed distally of the free end of the deflectable arm, and the first locking member is out of engagement with the second locking member;

release the needle sleeve, the biasing element pushes the needle sleeve in a distal direction, the inwardly projecting boss disengaging from the second locking member, the second locking member moving to a relaxed position, thereby rendering the needle sleeve is in a start position in which the first locking member is disposed distally of the free end of the deflectable arm and the second locking member is in the relaxed position.

Enabling the priming of the locking mechanism to be carried out during assembly of the device by machinery as opposed to manually may be beneficial for those who are elderly or infirm, or for those who are in a rush or require easier actuation of the device. The needle sleeve being in the start position may simplify actuation of the injection device for a user.

The method may comprise inserting the carrier into a sub-assembly comprising the housing and needle sleeve into an intermediate position before moving the needle sleeve relative to the housing into the first assembly position, and subsequently moving the carrier further within the housing is a distal direction to the second assembly position after the needle sleeve have been moved into the first assembly position.

In one embodiment the second locking member may have two deflectable arms; the deflectable arms may each have a first end fixedly attached to the rest of the needle sleeve and a second end which is free. In the second assembly position the first locking member may be disposed between the two arms.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which:

FIG. 1A is a schematic side view of an auto-injector;

FIG. 1B is a schematic side view of the auto-injector of FIG. 1A, with some internal components shown;

DETAILED DESCRIPTION

Figure 2:
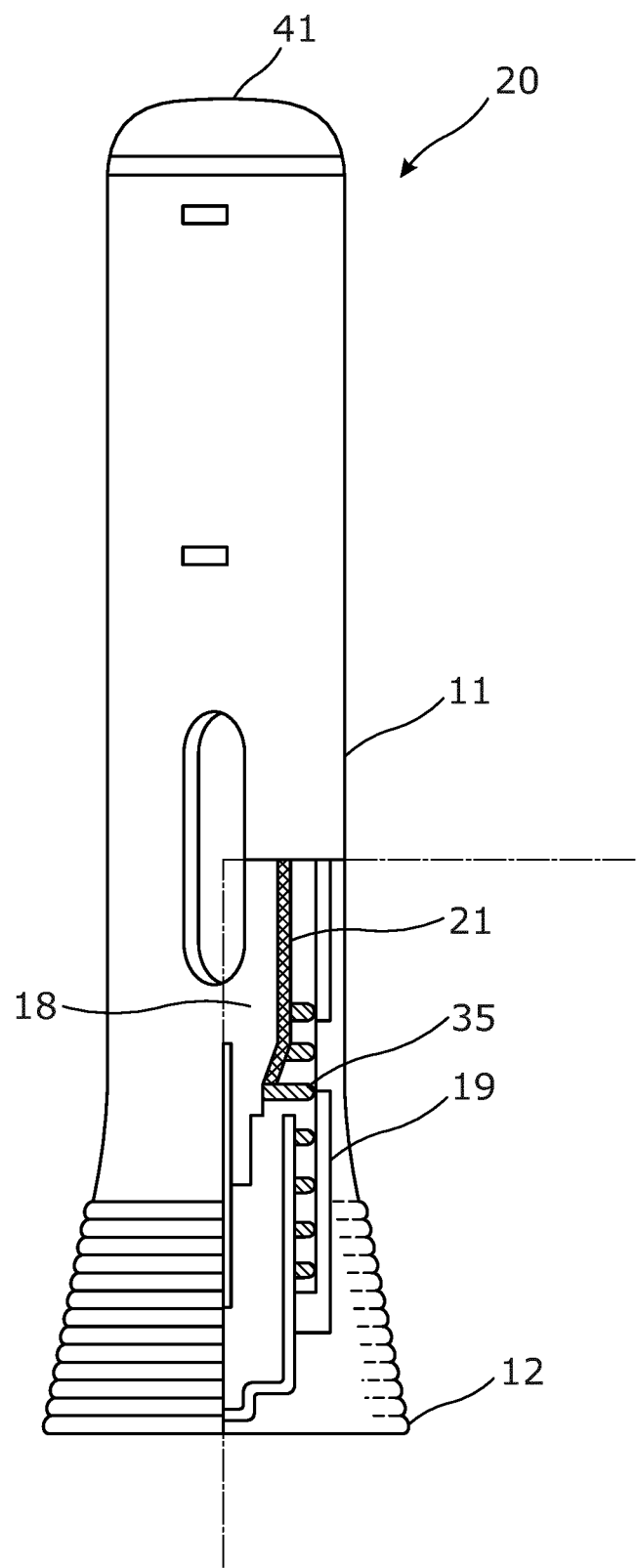
FIG. 2 is a side view of an injection device having a locking mechanism, with a corner cut out to illustrate some of the internal components.
Figure 3:
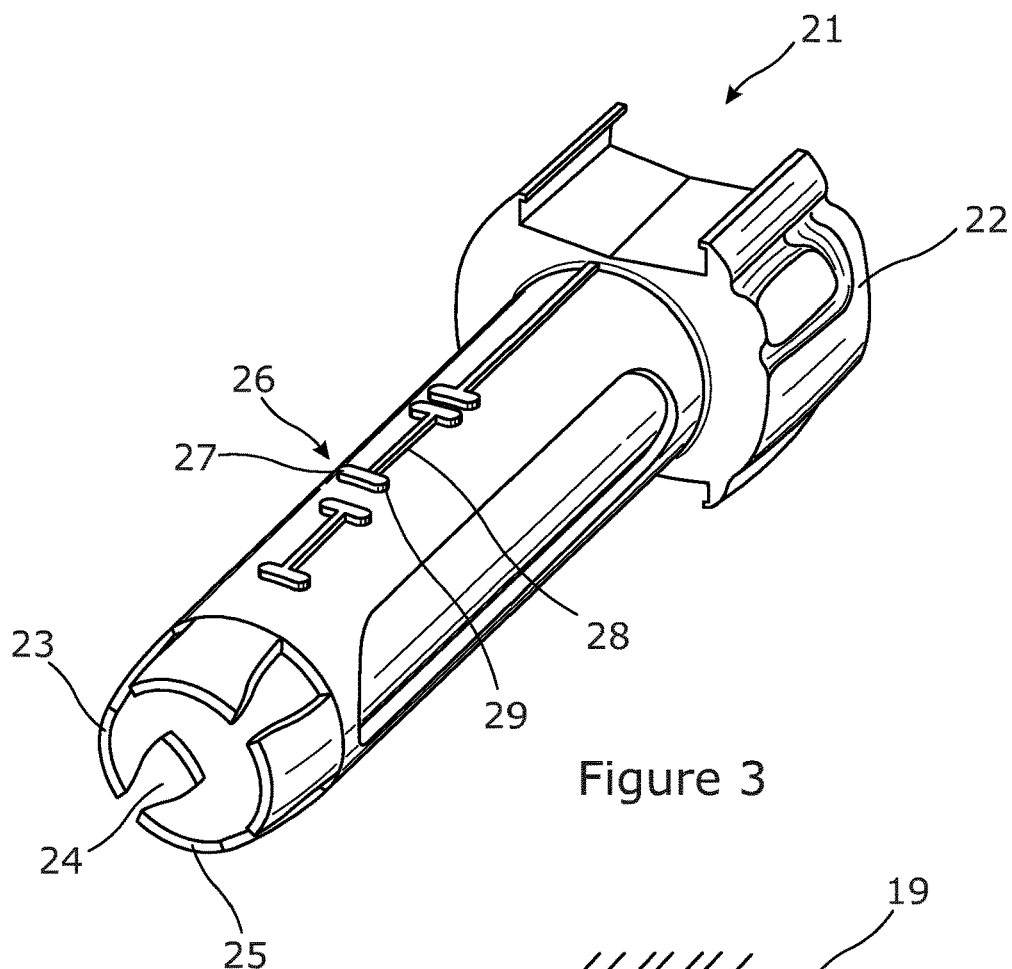
FIG. 3 is a perspective view of a carrier of FIG. 2.
Figure 4:
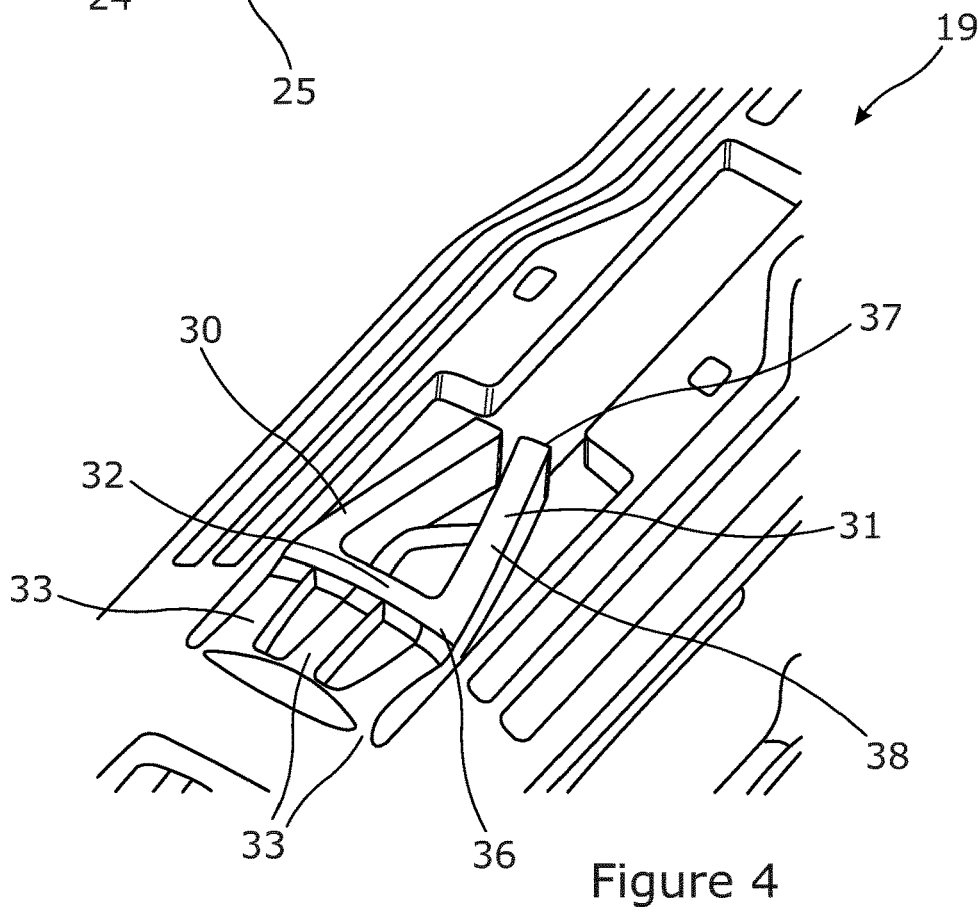
FIG. 4 is a perspective view of a portion of a needle sleeve of FIG. 2 showing a second locking member in a relaxed position.
Figure 5:
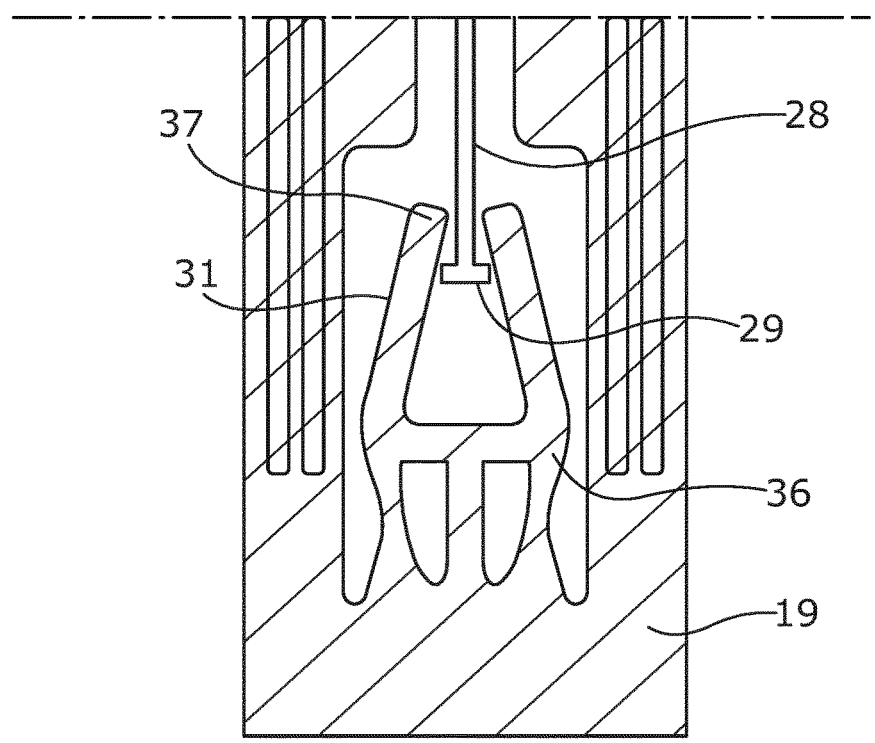
FIG. 5 is a close up view of the locking mechanism when the needle sleeve is in a start position.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle sleeve in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of needle sleeve 19 relative to housing 11. For example, needle sleeve 19 can move in a longitudinal direction parallel to longitudinal axis A-A.

Specifically, movement of needle sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of needle sleeve 19 by placing a distal end of needle sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to needle sleeve 19.

Another form of insertion is "automated," whereby needle 17 moves relative to housing 11. Such insertion can be triggered by movement of needle sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within needle sleeve 19 or housing 11. Retraction can occur when needle sleeve 19 moves distally as a user removes device 10 from a patient's body. This can occur as needle 17 remains fixedly located relative to housing 11. Once a distal end of needle sleeve 19 has moved past a distal end of needle 17, and needle 17 is covered, needle sleeve 19 can be locked.

As the locking of the needle sleeve is based on a relative movement between the housing or needle and the needle sleeve, the length of the needle needs to be taken into account when considering a suitable locking mechanism. There are a number of benefits to using a short needle in an injection device; the overall size of the device is reduced in comparison to devices with longer length needles, the injection time can be improved, more viscous fluids can be injected, storage loads and stopper impact forces can be reduced and a thinner gauge needle can be used without compromising the injection time. A thinner gauge needle may also mean that there is less pain for a user and could be particularly beneficial in pediatric applications.

'Short' when referred to in this specification refers to a length of less than about 12.5 mm, typically as an example about 6 mm, however it can be appreciated that the device described below can also be used for a needle length greater than or equal to 12.5 mm. The length of the needle 17 can be measured from the distal end of the syringe 18 glass to the tip of the needle 17.

Referring now to FIGS. 2 to 10, an injection device 20 according to a first embodiment of the disclosure is shown. The injection device 20 is in the form of an auto-injector 20 that has similar features to the auto-injector 10 described above in relation to FIGS. 1A and 1B, with like features retaining the same reference numerals. The device 20 has a carrier 21 comprising a receiving end 22 for receiving a syringe, and a needle end 23, through which a needle 17 of the syringe protrudes when received in the carrier 21. The receiving end 22 is larger than the needle end 23, the needle end 23 further comprising cut out portions 24, and carrier sections 25 tapering towards a distal end of the carrier. The carrier 21 further comprises a first locking member 26 which consists of at least one substantially rigid boss or protrusion 27. This carrier boss 27 has a body portion 28 and a head portion 29, however it can be appreciated that only the head portion is required in some cases. The head portion 29 is substantially T shaped and the body portion 28 is substantially linear. However it can be appreciated by a personal skilled in the art that the head portion 29 could be any alternative shape, for example but not limited to an arrow head shape, a V shape, an arc or hook shape. The body portion 28 can also be non-linear.

For the assembly of the injection device 20 the carrier 21 is inserted into a sub assembly comprising the needle sleeve 19 and the housing 11. It can be appreciated that the carrier, needle sleeve and housing are all assembled as part of the same stage. The needle sleeve 19 comprises needle sleeve legs 39 and cut away portions 40. The needle sleeve 19 further comprises a second locking member 30 comprising a pair of deflectable arms 31 attached to each other by a strut 32. The strut is then coupled to the rest of the needle sleeve 19 by three supports 33. The deflectable arms 31, strut 32 and supports 33 can all be integrally formed with the needle sleeve 19, it can also be appreciated that these may be any combination of separate parts coupled to one another. The deflectable arms may be coupled directly to the needle sleeve 19 and no further struts 32 or supports 33 may be required. There may also be more or less than three supports 33, or more or less than one strut 32 depending on the structural properties required from the second locking member 30. The needle sleeve 19 can have a pair of second locking members 30 disposed on opposite sides of the needle sleeve 19.

The deflectable arms 31 have a first end 36 fixedly attached to the rest of the needle sleeve 19 and a second, opposite end 37 extending from the first end in a proximal direction. The second end 37 is free and not attached to the rest of the needle shield other than via the first end 36. The deflectable arms also have an intermediate part 38 which can be straight, bent inwards towards each other or comprise a further joint.

Figure 6:
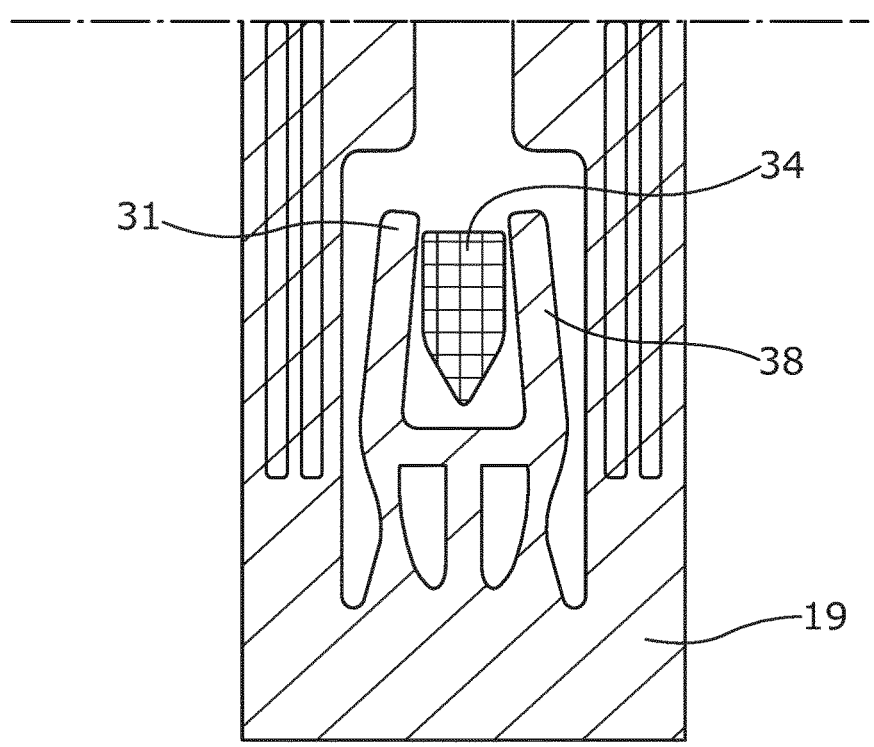
FIG. 6 is a close up view of the locking mechanism when the needle sleeve is in a retracted position.
Figure 7:
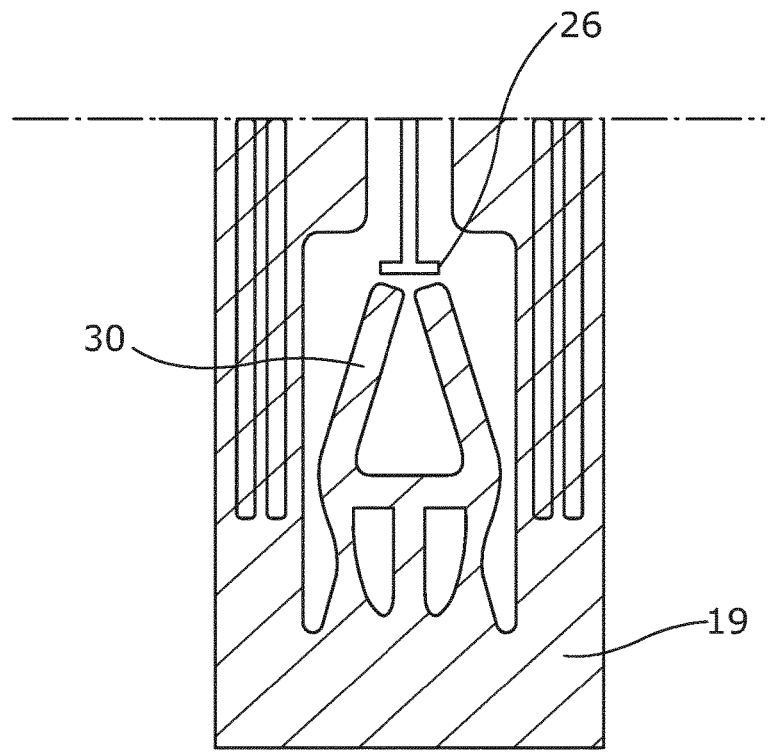
FIG. 7 is a close up view of the locking mechanism when the needle sleeve is in an extended position.
Figure 8:
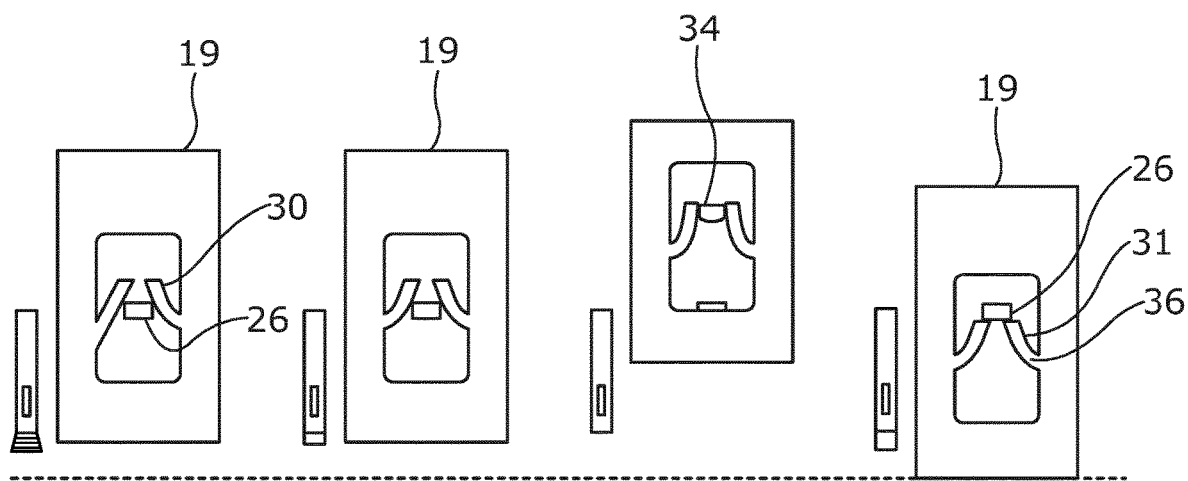
FIG. 8 is a diagram of the different stages of the locking mechanism during use of the device of FIG. 2.
Figure 9:
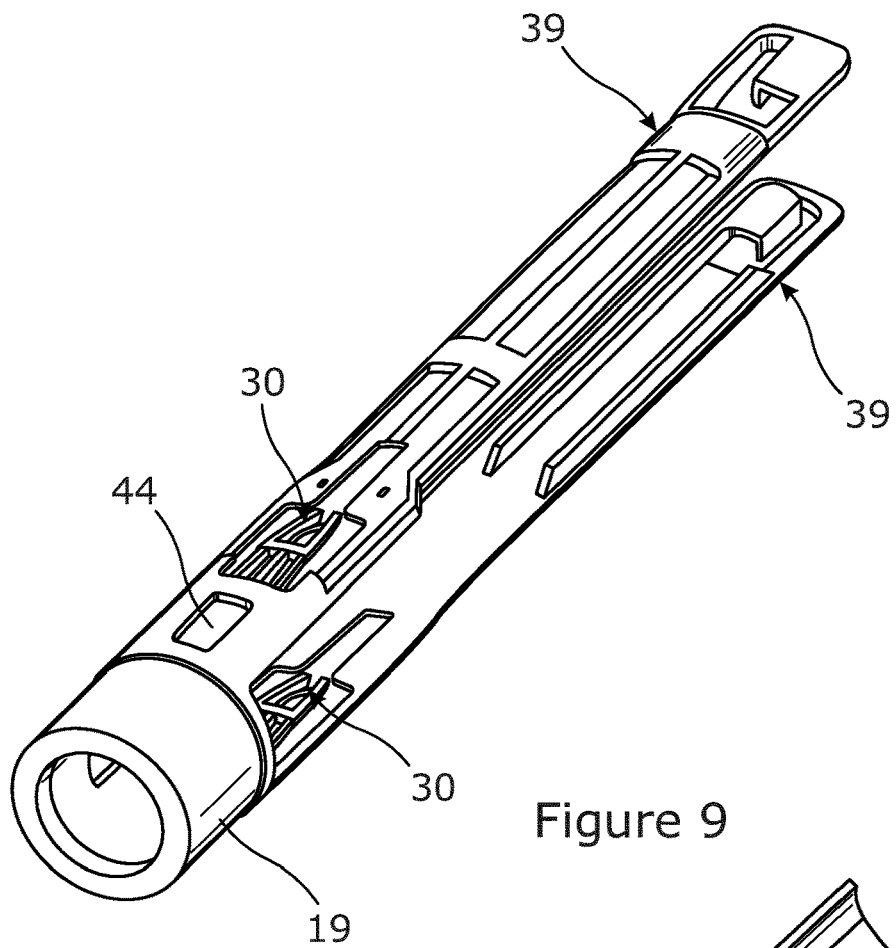
FIG. 9 is a perspective view of the needle sleeve of the device of FIG. 2.
Figure 10:
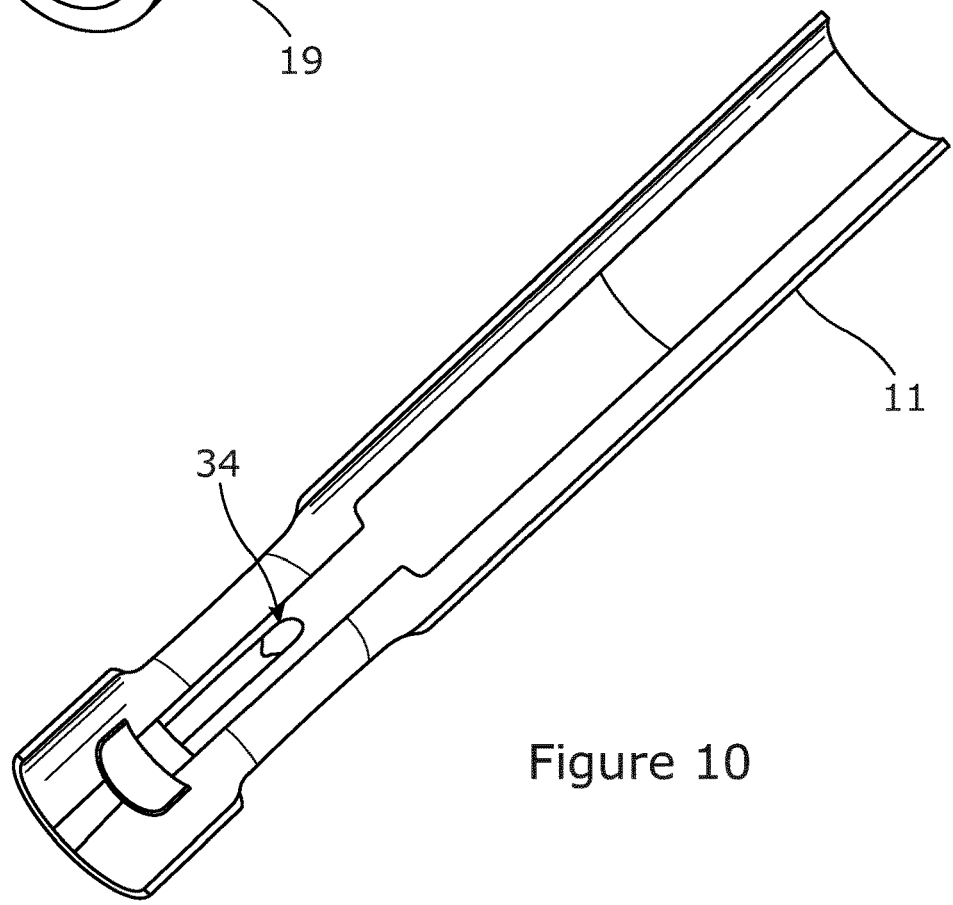
FIG. 10 is a perspective view of the housing of the device of FIG. 2.

The housing 11 further comprises an inwardly projecting boss 34 located towards a distal end of the housing 11. The inwardly projecting boss 34 can be tapered pointing towards a distal end of the injection device 20. The inwardly projecting boss 34 may be integrally formed with the housing 11, however it can be appreciated that the inwardly projecting boss 34 may be a separate component coupled to the housing 11. The inwardly projecting boss 34 is to engage with the second locking member 30, forcibly moving the deflectable arms 31 apart, opening the space between the two deflectable arms into a deflected position as shown in FIG. 6. This engagement between the second locking member 30 of the needle sleeve 19 and the inwardly projecting boss 34 of the housing can be actuated by the needle sleeve 19 being moved in a proximal direction with respect to the housing 11. When the inwardly projecting boss 34 is not engaged with the second locking member 30 then the second locking member is in a relaxed position as shown in FIG. 7.

When the second locking member 30 is in a deflected position as shown in FIG. 6 the first locking member 26 and in particular the carrier boss 27 is able to move past the free ends 37 of the deflectable arms 31. When the second locking member 30 is in a relaxed position the head portion 29 of the first locking member is unable to pass the free ends 37 of the deflectable arms 31. In a relaxed position either the head portion 29 is trapped between the deflectable arms 31 of the second locking member 30 and is restricted from axial movement in a proximal direction past the deflectable arms 31 or the head portion is stopped by the free ends 37 of the deflectable arms 31 of the second locking member and restricted from axial movement in a distal direction past the deflectable arms 31. The movement described above is relative to the housing.

To assemble the device 20 the needle sleeve is inserted into the housing and the syringe 17 is inserted into the carrier 21. The carrier 21 and syringe 18 are advanced to an intermediate position within the housing 11, an intermediate positon being less than fully inserted into the device and can be known as a first assembly position. The needle sleeve 19 is then moved in a proximal direction with respect to the housing 11 pushing the deflectable arms 31 towards the inwardly projecting boss 34 opening the second locking member 30 into the deflected position. The carrier 21 can then be moved further in the distal direction, the carrier boss 27 being able to pass the deflectable arms 31 as they are opened by the inwardly projecting boss 34. This can be known as the second assembly position and can be the final assembled position for the carrier 21 and syringe. It can however be envisaged that the intermediate position is not required and the carrier 21 can be fully inserted at the same time as the needle sleeve 19 has been depressed and the deflectable arms 31 are in the deflected position. The rest of the device is then assembled, such as the insertion of a drive assembly into the housing to prepare the device for use. The drive assembly comprises a plunger 15, a drive spring 46 and a housing end 41. The drive spring 46 is arranged to push the plunger 15 acting on the piston 14 into the syringe 18 to force medicament through the needle 17 during use of the injector device 10. The plunger 15 and piston 14 may be separate components or a single component.

Figure 11:
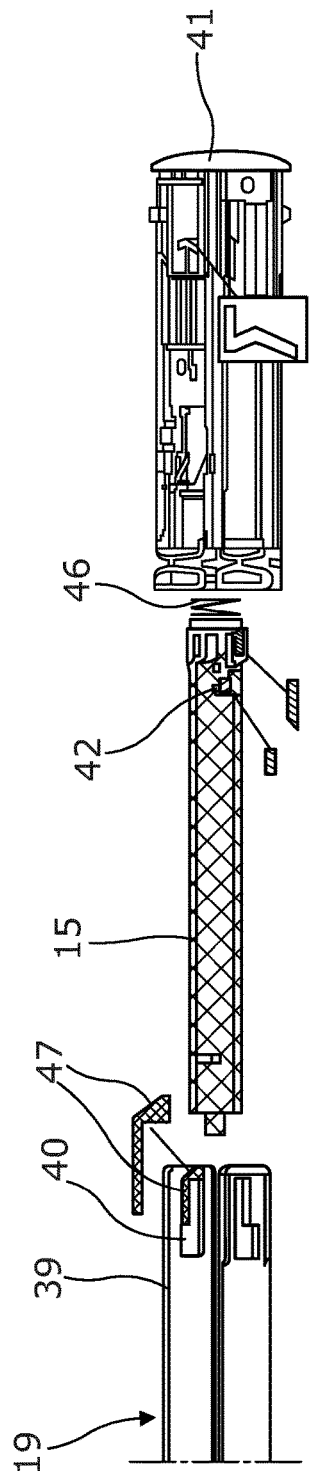
FIG. 11 is a side view of a needle sleeve, plunger and an end of the housing of FIG. 2.
Figure 12:
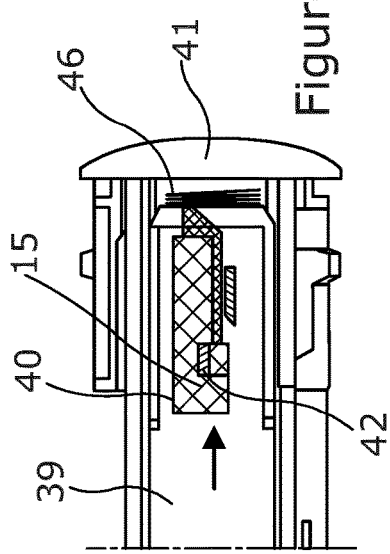
FIG. 12 is a side view of the components of FIG. 11 assembled in a start position.

During assembly the plunger is rotated as it is inserted into the device either manually or by a suitable assembly tool and a plunger boss 42 engages with a needle sleeve rib 47 on the needle sleeve legs 39 as can be seen in FIGS. 11 and 12. The needle sleeve 19 is held in a retracted position while the drive assembly is inserted and then let go, when the it is let go the needle sleeve 19 moves in a distal direction, however the engagement between the plunger boss 42 and the needle sleeve rib 47 during the assembly and priming of the device prevents the needle sleeve 19 from fully extending into the extended position. The contact between the plunger boss 42 and the needle sleeve rib 47 also prevents downward rotation of the plunger in this position. When the needle sleeve 19 is depressed or moved into the retracted position for an injection the plunger is able to rotate further and the plunger boss 42 disengages with the rib 47, the needle sleeve is then free to move into the extended position and the plunger is free to move distally under the force of the drive spring to dispense the medicament.

It can be appreciated that the needle sleeve can be held in the start position by alternative means, for example the needle sleeve could engage with protrusions or retractable parts of the housing. The retractable parts being retracted by an actuator after an injection has occurred. Furthermore the needle sleeve can be held in the start position by a further component such as a collar located at a distal end of the device, the needle sleeve comprising protrusions which engage with slots in the collar, the collar rotating as an injection occurs in a similar manner to the plunger 15 during the assembly stage to release the needle sleeve into a fully extended position once the injection is complete. It can be appreciated that a person skilled in the art can determine a number of alternative methods to simply catch and release two components.

When the device 20 is fully assembled the needle sleeve 19 is released or moved in a distal direction disengaging from the inwardly projecting boss 34 into a start position, the head portion 29 of the carrier boss 27 remains distally of the free ends 37 of the deflectable arms 31 and the needle sleeve is not fully extended due to the engagement with the plunger 15 described above. This arrangement means the device is now assembled and primed for use by a user.

Figure 13:
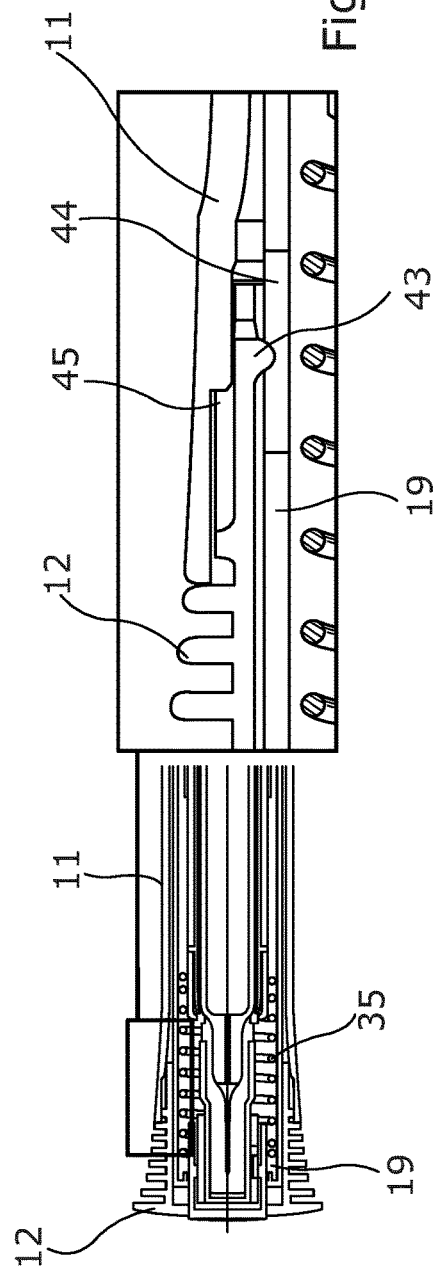
FIG. 13 is a close up schematic side view of a cap and needle sleeve of the device of FIG. 2.

To use the device 20, the cap 12 is removed from the rest of the device, in particular from the housing 11, however it can be appreciated that the device 20 may not have a cap assembly or it may have already been removed. The cap also reduces the risk of accidental actuation of the injection device, for example when the device is dropped. As can be seen in FIG. 13 when the cap 12 is on the device, a locking boss 43 on the cap 12 may engage with corresponding cut outs 44 on the needle sleeve 19 preventing accidental depression of the needle sleeve 19 before the cap 12 is removed. As the cap 12 is removed the locking boss 43 is able to elastically deform into a stepped portion 45 of the housing 11, releasing the locking boss 43 from the needle sleeve cut outs 44. After the cap is removed the needle is then inserted into the body of the patient at the injection site to dispense a medicament, the needle sleeve 19 being depressed in a proximal direction in the process from the start position to the retracted position. During this process the needle sleeve 19 is moved in a proximal direction against a biasing force of a biasing means, for example a spring 35, into the retracted position. In the retracted position the second locking portion engages with the inwardly projecting boss 34, the inwardly projecting boss is shaped to push against the deflectable arms, moving the second locking portion into the deflected position wherein the two deflectable arms deflect laterally of the central axis of the device from a proximal to a distal end. The spring biases the needle sleeve 19 in a distal direction and towards the extended position. However it can be appreciated that the biasing means could be an alternative for example a bellows or compressed foam, or the sleeve could be moved into the extended position by a magnetic attraction or repelling means.

In the extended position the first locking member is not engaged with the second locking member and the head portion 29 is on a proximal side of the deflectable arms, the second locking portion is in a relaxed position and the spring 35 pushes the needle sleeve 19 into the extended position. When the needle sleeve is in the extended position, after an injection has occurred, if the needle sleeve 19 is depressed or moved in a proximal direction then the second locking member abuts the head portion 29 of the carrier boss 27 preventing axial movement in a proximal direction of the needle sleeve 19 in relation to the carrier 21. If a force is applied to the needle sleeve 19 in the proximal direction when the needle sleeve is in the extended position then the load is resolved through the interface between the free ends of the deflectable arms 31 and the carrier boss 27. This mechanism can improve the safety of the device as the mechanism effectively locks the needle sleeve 19 in the extended position enclosing the needle 17, ensuring that a user cannot access the needle 17 after injection is complete.

It can be appreciated that the second locking member may comprise only one deflectable arm located against a surface of the needle sleeve 19, it may also comprise a deflectable member of an alternative shape for example a cup shaped deflectable member with a corresponding T shaped head portion 29 or any alternative deflectable member with a correspondingly shaped head portion 29. There are a number of alternative deflectable or flexible members or arms which can trap and block a rigid carrier boss as described above.

The deflectable members and arms can be made of a flexible material, however they may also include joints, pivots or hinges to deflect and can therefore be flexible or substantially rigid.

It can be appreciated that the carrier boss 27 can have flexible properties in that it may be the shape of the carrier boss 27 when engaged with the second locking member 30 which causes it to be trapped and stopped by the deflectable arms.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injection device comprising:
   a housing;
   a carrier disposed within the housing for holding a syringe that has a needle at one end;
   a needle sleeve located within the housing and being axially moveable with respect to the housing between an extended position and a retracted position;
   a biasing element configured to bias the needle sleeve towards the extended position; and
   a locking mechanism configured to lock the needle sleeve in the extended position after an injection of a medicament by the injection device, the locking mechanism comprising (i) a first locking member provided on and projecting from the carrier and (ii) a second locking member comprising a deflectable arm provided on the needle sleeve and moveable between a relaxed position and a deflected position;
   wherein the housing includes an inwardly projecting boss configured to engage the second locking member and configured to move the second locking member into the deflected position as the needle sleeve is moved to the retracted position;
   wherein the first locking member is out of engagement with the second locking member when the second locking member is in the deflected position; and wherein the second locking member blocks the first locking member when the second locking member is in the relaxed position and the needle sleeve is in the extended position to prevent movement of the needle sleeve back into the retracted position.

2. The injection device according to claim 1, wherein the needle sleeve extends further from the housing in the extended position than in the retracted position.

3. The injection device according to claim 1, wherein the deflectable arm has a first end fixedly attached to a body of the needle sleeve and a free end remote from the first end.

4. The injection device according to claim 3, wherein the free end of the deflectable arm extends in a proximal direction from the first end of the deflectable arm.

5. The injection device according to claim 1, wherein the needle sleeve is moveable between three positions: (i) a start position, (ii) the retracted position, and (iii) the extended position, wherein the needle sleeve extends further from the housing in the extended position than in the start position, and wherein the needle sleeve extends further from the housing in the start position than in the retracted position.

6. The injection device according to claim 5, wherein, in the start position, the deflectable arm is in the relaxed position and the first locking member is disposed distally of a free end of the deflectable arm.

7. The injection device according to claim 1, wherein the first and second locking members are axially aligned when the second locking member is in the relaxed position and are out of axial alignment when the second locking member is in the deflected position.

8. The injection device according to claim 1, wherein the deflectable arm is deflectable laterally with respect to an axial direction of the injection device when the second locking member is engaged by the inwardly projecting boss of the housing.

9. The injection device according to claim 1, wherein the second locking member comprises a pair of deflectable arms.

10. An injection device according to claim 1, wherein the injection device further comprises a removable cap.

11. The injection device according to claim 1, wherein the first locking member comprises a T shaped boss projecting from the carrier.

12. The injection device according to claim 11, wherein a head of the T shaped boss is configured to be (i) held or blocked by the second locking member when the second locking member is in the relaxed position and (ii) movable past the second locking member when the second locking member is in the deflected position.

13. The injection device according to claim 1, wherein the inwardly projecting boss of the housing is tapered and points in a distal direction.

14. The injection device according to claim 13, wherein the inwardly tapered projecting boss is configured to force the second locking member into the deflected position when the needle sleeve is in the retracted position and release the second locking member into the relaxed position when the needle sleeve is in the extended position.

15. The injection device according to claim 1, further comprising the syringe having the needle at one end.

16. The injection device according to claim 15, wherein the syringe contains the medicament.

17. The injection device according to claim 15, wherein the needle comprises a length of less than 12.5 mm measured from a distal end of the syringe to a tip of the needle.

18. The injection device according to claim 1, wherein the first locking member comprises at least one rigid portion and the second locking member comprises at least one flexible portion.

19. The injection device according to claim 1, wherein the first locking member comprises a boss projecting from the carrier and the boss is configured to be (i) held or blocked by the second locking member when the second locking member is in the relaxed position and (ii) movable past the second locking member when the second locking member is in the deflected position.

20. A method of assembling an injection device, comprising:
inserting a syringe having a needle into a carrier of the injection device, the injection device comprising a first locking member provided on and projecting from the carrier;
moving a needle sleeve relative to a housing in a proximal direction of the injection device to a first assembly position such that an inwardly projecting boss of the housing engages a second locking member comprising a deflectable arm provided on the needle sleeve and move the second locking member from a relaxed position into a deflected position;
moving the carrier into the housing in a distal direction to a second assembly position in which (i) the second locking member is in the deflected position, (ii) the first locking member is disposed distally of a free end of the deflectable arm, and (iii) the first locking member is out of engagement with the second locking member;
releasing the needle sleeve such that a biasing element pushes the needle sleeve in the distal direction, the inwardly projecting boss disengaging from the second locking member, the second locking member moving to the relaxed position such that the needle sleeve is in a start position in which the first locking member is disposed distally of the free end of the deflectable arm and the second locking member is in the relaxed position.

* * * * *